(12) United States Patent
Kuczynski et al.

(10) Patent No.: US 8,950,239 B2
(45) Date of Patent: Feb. 10, 2015

(54) CONDUCTIVE DUST DETECTION

(75) Inventors: Joseph Kuczynski, Rochester, MN (US); Melissa K. Miller, Research Triangle Park, NC (US); Prabjit Singh, Poughkeepsie, NY (US); Heidi D. Williams, Cary, NC (US); Jing Zhang, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 210 days.

(21) Appl. No.: 13/351,693

(22) Filed: Jan. 17, 2012

(65) Prior Publication Data

US 2013/0180271 A1    Jul. 18, 2013

(51) Int. Cl.
| | | |
|---|---|---|
| *G01N 37/00* | (2006.01) | |
| *G01G 23/01* | (2006.01) | |
| *G01L 25/00* | (2006.01) | |
| *G01G 19/56* | (2006.01) | |
| *G01N 19/00* | (2006.01) | |
| *G01N 21/81* | (2006.01) | |
| *G01M 15/00* | (2006.01) | |
| *G01F 3/04* | (2006.01) | |

(52) U.S. Cl.
USPC ..... 73/28.01; 73/1.11; 73/335.01; 73/114.58; 73/261

(58) Field of Classification Search
CPC ....... G01F 3/10; G01F 15/066; G01L 25/003; G01N 21/3504; G01M 15/042; A47L 2201/06; A47L 9/2894; A47L 2201/00; A47L 9/19; A47L 9/2857; H01L 29/1608; H01L 29/7869; H01L 21/02554; H01L 21/046; H01L 29/0649
USPC .............. 73/28.01, 1.11, 335.01, 114.58, 261
See application file for complete search history.

(56) References Cited

U.S. PATENT DOCUMENTS

| | | | |
|---|---|---|---|
| 4,988,877 A * | 1/1991 | Stokowksi et al. | ........ 250/358.1 |
| 5,247,827 A | 9/1993 | Shah | |
| 5,457,396 A | 10/1995 | Mori et al. | |
| 5,525,804 A * | 6/1996 | MacArthur et al. | .......... 250/374 |
| 5,910,700 A | 6/1999 | Crotzer | |
| 7,041,153 B2 * | 5/2006 | Totoki | ................................ 95/3 |

(Continued)

FOREIGN PATENT DOCUMENTS

| | | |
|---|---|---|
| WO | WO 2008/025602 A1 | 3/2008 |
| WO | WO 2009/010389 A1 | 1/2009 |

*Primary Examiner* — Peter Macchiarolo
*Assistant Examiner* — Mohammed Keramet-Amircola
(74) *Attorney, Agent, or Firm* — Margaret A. McNamara, Esq.; Kevin P. Radigan, Esq.; Heslin Rothenberg Farley & Mesiti P.C.

(57) ABSTRACT

An apparatus is provided, which includes a dust detector, a voltage source, and a controller. The dust detector includes two opposing surfaces and a conductive dust sensor. The two opposing surfaces are disposed in spaced, opposing relation to allow for the passage of airflow between the surfaces, and the conductive dust sensor is disposed at a surface of the two opposing surfaces. The voltage source is configured and controlled to establish an electrostatic field at least partially between the two opposing surfaces to facilitate directing conductive particles in the airflow passing between the two opposing surfaces towards the dust sensor. The controller monitors for a leakage current within the conductive dust sensor and determines whether the leakage current exceeds a predetermined trigger level indicative of the presence of conductive dust, and if so, automatically indicates a conductive dust warning.

20 Claims, 9 Drawing Sheets

(56) References Cited

U.S. PATENT DOCUMENTS

| | | | |
|---|---|---|---|
| 7,109,722 B2 * | 9/2006 | Chamberlin et al. | 324/551 |
| 7,385,195 B2 * | 6/2008 | Yamada et al. | 250/307 |
| 7,610,794 B2 | 11/2009 | Yamaguchi et al. | |
| 2003/0147785 A1 * | 8/2003 | Joannou | 422/186.04 |
| 2006/0278080 A1 * | 12/2006 | Li et al. | 96/18 |
| 2009/0229784 A1 * | 9/2009 | Rohr | 165/11.1 |
| 2012/0038366 A1 * | 2/2012 | Froman | 324/537 |
| 2012/0286172 A1 * | 11/2012 | Coulson et al. | 250/489 |

\* cited by examiner

CONDUCTIVE DUST DETECTION

BACKGROUND

In many large server applications, processors along with their associated electronics (e.g., memory, disk drives, power supplies, etc.) are packaged in removable node configurations stacked within an electronics (or IT) rack or frame. In other cases, the electronics may be in fixed locations within the rack or frame. Typically, the components are cooled by air-moving in parallel airflow paths, usually front-to-back, impelled by one or more air-moving devices (e.g., fans or blowers). The power dissipation of integrated circuit chips, and the modules containing the chips, continues to increase in order to achieve increases in processor performance. This trend poses challenges at both the module and system level. In certain cases it may be possible to handle increased power dissipation within a single node by providing greater airflow, through the use of a more powerful air-moving device or by increasing the rotational speed (i.e., RPMs) of an existing air-moving device.

Conductive dust may be entrained within the airflow passing through the electronics rack. Within a data center, this conductive dust can include, for example, salt contaminants that have a deliquescent relative humidity above which the salt will absorb moisture, become wet and create ionic bridges, which may potentially cause short circuiting of one or more electronic components within the rack. For example, conductive dust can cause electrical short circuiting of closely spaced electrical features on circuit boards or other components with exposed metal traces, and thereby degrade system reliability. Dust arises from several origins, including outdoor air, industrial operations, data center air conditioners, hardware corrosion (e.g., blower fretting corrosion), etc. Most dust contains one or more of C, Si, Ca, O, Al, K, S, Cl, and sometimes Fe. The most harmful dust particles are generally high in sulfur and chlorine-bearing salts. If the dust is found to be conductive at the existing relative humidity level, then component damage may occur, and the data center might need to be cleaned and any failed system hardware replaced.

BRIEF SUMMARY

The shortcomings of the prior art are overcome and additional advantages are provided through the provision of an apparatus which comprises a dust detector, a voltage source and a controller. The dust detector includes: two opposing surfaces disposed in spaced, opposing relation with a gap therebetween to facilitate passage of an airflow between the two opposing surfaces; and a conductive dust sensor, disposed at one surface of the two opposing surfaces. The voltage source establishes an electrostatic field at least partially between the two opposing surfaces, wherein the electrostatic field facilitates directing, at least in part, conductive particles in the airflow passing between the two opposing surfaces towards the conductive dust sensor. The controller monitors for a leakage current within the conductive dust sensor, and determines whether the leakage current exceeds a predetermined trigger level indicative of the presence of conductive dust, and responsive to the leakage current exceeding the predetermined trigger level, automatically indicates a conductive dust warning.

In another aspect, an electronics rack is provided which includes at least one air-moving device to establish an airflow through the electronics rack, and a monitoring apparatus associated with the electronics rack. The monitoring apparatus includes: a dust detector, which comprises two opposing surfaces disposed in spaced, opposing relation to facilitate passage of a portion of the airflow therebetween, and a conductive dust sensor, the conductive dust sensor being disposed at one surface of the two opposing surfaces; a voltage source to establish an electrostatic field at least partially between the two opposing surfaces, the electrostatic field facilitating directing, at least in part, conductive particles in the portion of the airflow passing between the two opposing surfaces towards the conductive dust sensor; and a controller which monitors for a leakage current within the conductive dust sensor, and determines whether the leakage current exceeds a predetermined trigger level indicative of the presence of conductive dust. Responsive to the leakage current exceeding the predetermined trigger level, the controller automatically indicates a conductive dust warning.

In a further aspect, a monitoring method is provided which includes: associating a dust detector with an electronics rack, the dust detector including two opposing surfaces disposed in spaced, opposing relation with a gap therebetween to facilitate passage of an airflow between the two opposing surfaces; and a conductive dust sensor disposed at one surface of the two opposing surfaces; establishing an electrostatic field at least partially between the two opposing surfaces, the electrostatic field facilitating directing, at least in part, conductive particles in the airflow passing between the two opposing surfaces towards the conductive dust sensor; monitoring for a leakage current within the conductive dust sensor indicative of the presence of conductive dust, and determining whether the leakage current exceeds a predetermined trigger level; and responsive to the leakage current exceeding the predetermined trigger level, automatically indicating a conductive dust warning.

Additional features and advantages are realized through the techniques of the present invention. Other embodiments and aspects of the invention are described in detail herein and are considered a part of the claimed invention.

BRIEF DESCRIPTION OF THE SEVERAL VIEWS OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

DETAILED DESCRIPTION

As used herein, the term "electronics rack", includes any housing, frame, rack, compartment, blade server system, etc., having one or more heat generating components of a computer system or electronic system, and may be, for example, a stand-alone computer processor having high, mid or low end processing capability. In one embodiment, an electronics rack may comprise multiple electronic systems, each having one or more heat generating components disposed therein requiring cooling. "Electronic system" refers to any sub-housing, blade, book, drawer, node, compartment, etc., having one or more heat generating electronic components disposed therein. Each electronic system of an electronics rack may be movable or fixed relative to the electronics rack, with the central electronic complex (CEC) nodes of an IBM System z® mainframe computer being one example of electronic systems of an electronics rack. Further, "data center" refers to a computer installation containing one or more electronics racks. As a specific example, a data center may include one or more rows of rack-mounted computing units.

Reference is made below to the drawings, which are not drawn to scale to facilitate an understanding of the invention, wherein the same or similar reference numbers used throughout different figures designate the same or similar components.

Figure 1:
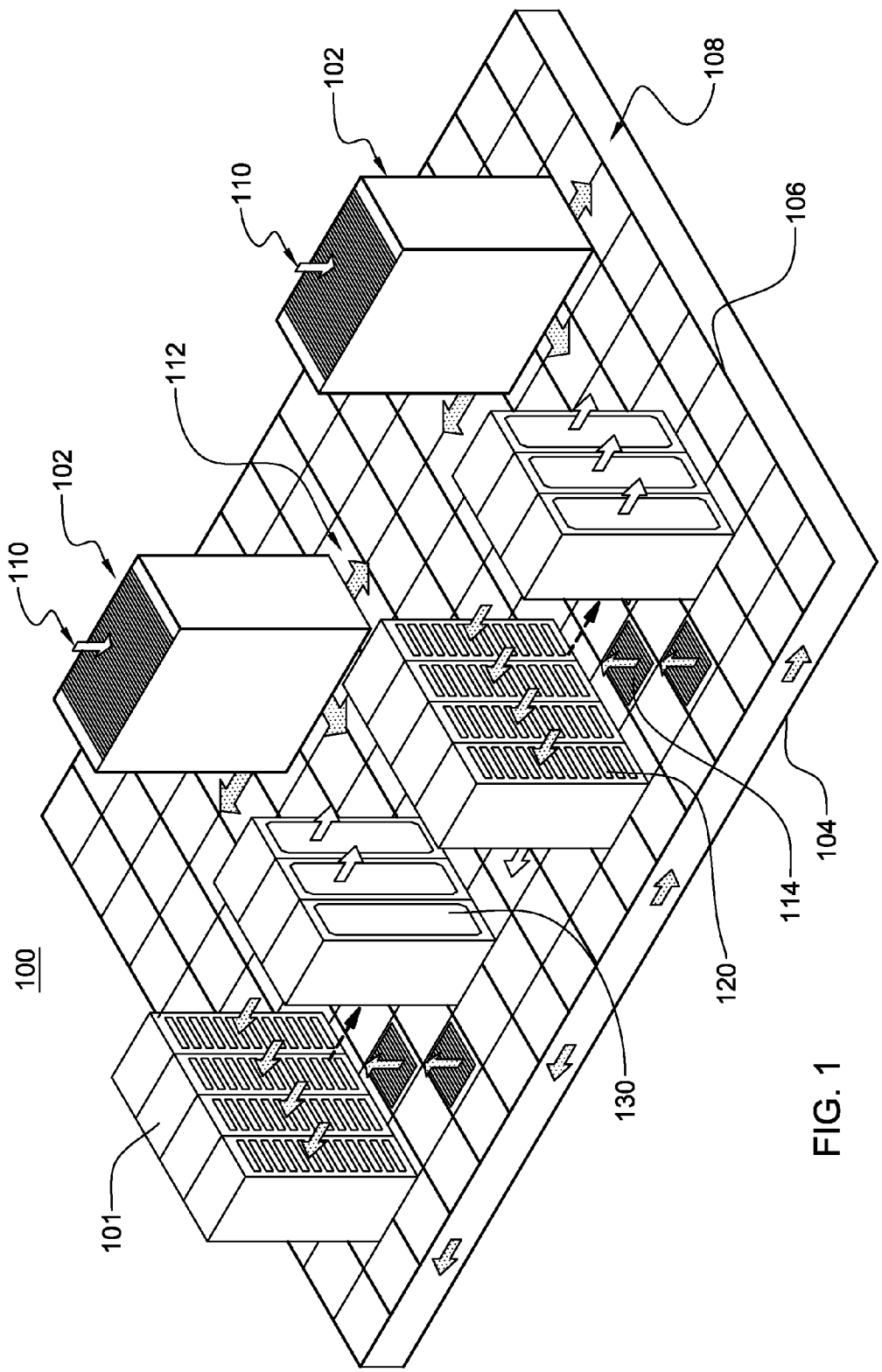
FIG. 1 depicts one embodiment of a conventional raised floor layout of an air-cooled data center.

FIG. 1 depicts one embodiment of a data center 100, which in the example depicted, is a raised floor layout of an air-cooled computer installation or data center 100. Data center 100 includes electronics (or information technology (IT)) racks 101 disposed in one or more rows on raised floor 106 of data center 100. One or more air-conditioning units 102 (also referred to as computer room air-conditioners (CRACs)) take in hot air (for example, through one or more air inlet vents in the top of the CRACs) and exhaust cooled air into a sub-floor plenum 108 below raised floor 106. Hot airflow through data center 100 is depicted by light arrows 110, and cooled airflow through data center 100 is indicated by stippled arrows 112.

In FIG. 1, electronics racks 101 employ a front-to-back cooling approach. Namely, according to this approach, cool air is drawn in through a front (air inlet side) 120 of each rack, and hot air is exhausted from a back (air outlet side) 130 of each rack. The cool air drawn into the front of the rack is supplied to air inlets of the electronic components (e.g., servers) disposed within the IT racks. Space between raised floor 106 and a sub-floor 104 defines the sub-floor plenum 108. Sub-floor plenum 108 serves as a conduit to transport, for example, cooled air from the air-conditioning units 102 to the electronics racks. In one embodiment, racks 101 are arranged in a hot aisle/cold aisle configuration, with their air inlet sides and air outlet sides disposed in alternating directions, as illustrated in FIG. 1. Cooled air 112 is provided through one or more perforated floor tiles 114 in raised floor 106 from sub-floor plenum 108 into the cold aisles of the data center. The cooled air is then drawn into electronics rack 101, via their inlets, and subsequently exhausted into the data center via one or more air outlets of the individual electronics racks into the hot aisles of the data center.

The air-conditioning units 102 typically receive chilled water from a refrigeration chiller plant (not shown). Each air-conditioning unit includes a blower motor to circulate air through the air-conditioning unit, and to provide the cooled air to the sub-floor plenum. As such, in most data centers, the air-conditioning units are simple heat exchangers consuming power needed to force the cooled air into the sub-floor plenum.

Figure 2:
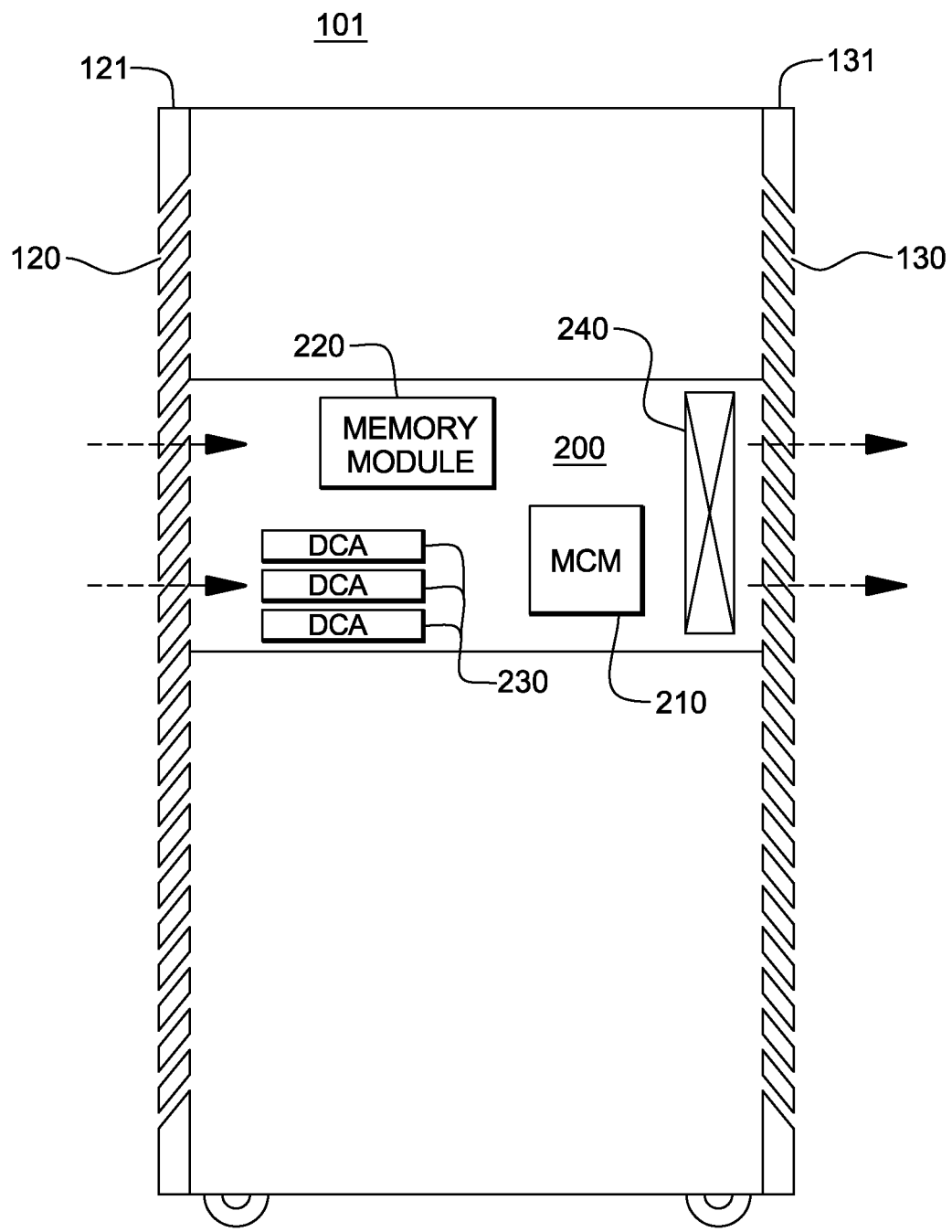
FIG. 2 is an elevational view of a partial embodiment of an electronics rack with an electronic system comprising multiple electronic components cooled by an airflow to be monitored for conductive dust, in accordance with one or more aspects of the present invention.

FIG. 2 depicts one embodiment of an electronics rack 101 having an electronic system 200 with one or more air-moving devices 240 associated therewith. As noted, by way of example, electronic system 200 might comprise a central electronics complex (CEC), such as provided with an IBM System z® mainframe computer (offered by International Business Machines Corporation, of Armonk, N.Y.). An IBM System z® mainframe computer may have one to four CECs disposed within one electronics rack, for example, arranged side-by-side within the rack.

Within electronic system 200, one or more multi-chip modules (MCM) 210 are disposed, along with supporting electronics for MCM(s) 210. The supporting electronics may include one or more memory modules 220, and multiple distributed converter assembly (DCA) power supplies 230. These electronic components are air-cooled in the embodiment illustrated employing one or more air-moving devices 240 (e.g., fans or blowers) positioned to move air across or through the electronic system, for example, from front (air inlet side) 120 to back (air outlet side) 130 of the rack 101, as illustrated in FIG. 2. In one embodiment, electronics rack 101 may include an air inlet door 121 and air outlet door 131, each of which is hingedly mounted to the frame of the electronics rack, to facilitate assembly and servicing of the electronic components within the electronics rack. In the embodiment illustrated, air inlet door 121 and air outlet door 131 are louvered to facilitate the ingress and egress, respectively, of external air through the electronics rack.

Figure 3:
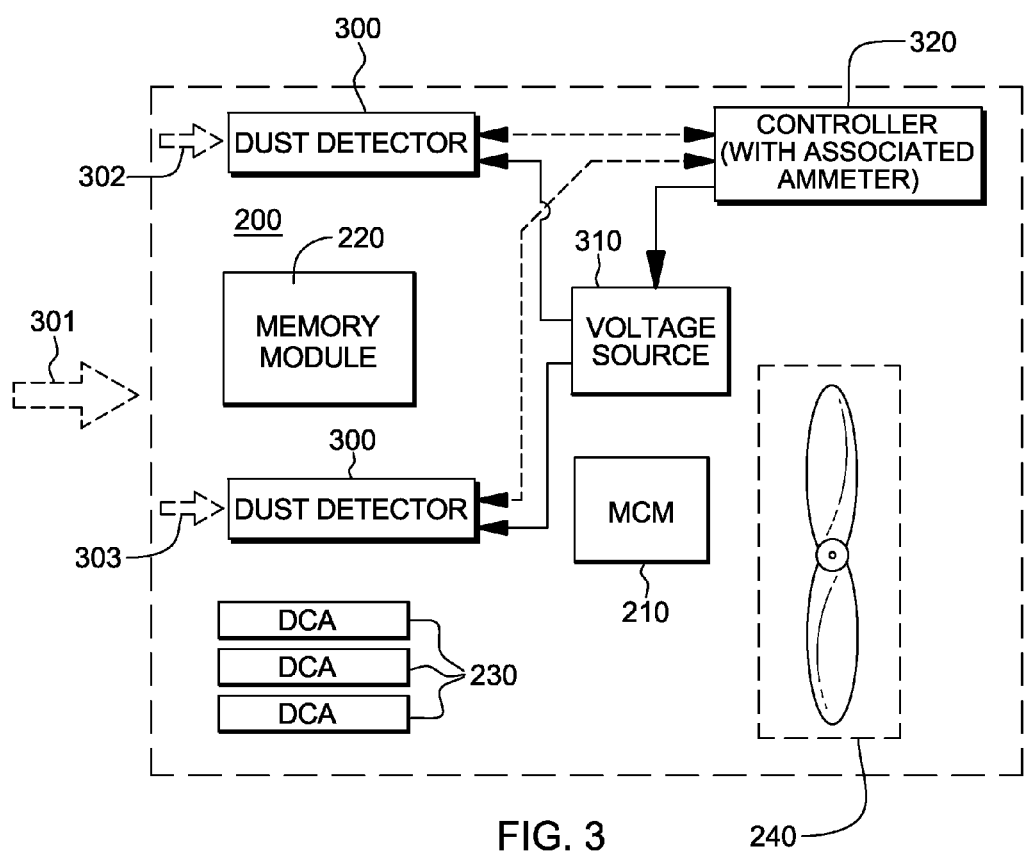
FIG. 3 is a schematic of the electronic system of FIG. 2, with one embodiment of a monitoring apparatus depicted for conductive dust monitoring, in accordance with one or more aspects of the present invention.

FIG. 3 depicts electronic system 200 of FIG. 2, and illustrates one embodiment of an early warning apparatus comprising one or more dust detectors 300, a voltage source 310, and a controller 320, in accordance with one or more aspects of the present invention. As described further below, controller 320 (depending on the implementation) controls voltage source 310 to apply an electrostatic field between the opposing surfaces of each dust detector, and a detection voltage to the dust detectors 300. Controller 320 may include one or more associated ammeters, which facilitate detection of leakage current within one or more conductive dust sensors of dust detectors 300. If desired, air-moving device(s) 240 could also be controlled by controller 320 to, for example, dynamically adjust the motor speed of the air-moving device(s) to account for a variety of ambient conditions including ambient temperature, altitude, heat load, configuration and motor variations.

In one embodiment, dust detectors 300 are disposed at or near the air inlet side of electronic system 200, so that portions 302, 303 of the airflow 301 passing through the electronic system also pass across (or through) the one or more dust detectors 300. Note that two dust detectors 300 are illustrated in FIG. 3 by way of example only. A single dust detector may be employed within a particular system, or three or more dust detectors could be employed, depending, for example, on the size of the system and the airflow rate through the system. Also, those skilled in the art should note that, although described herein as disposed within the electronic system and within an electronics rack, the early warning apparatus, including the dust detectors thereof, could be disposed anywhere within the data center, either internal or external to one or more electronics rack(s) within the data center.

Figure 4:
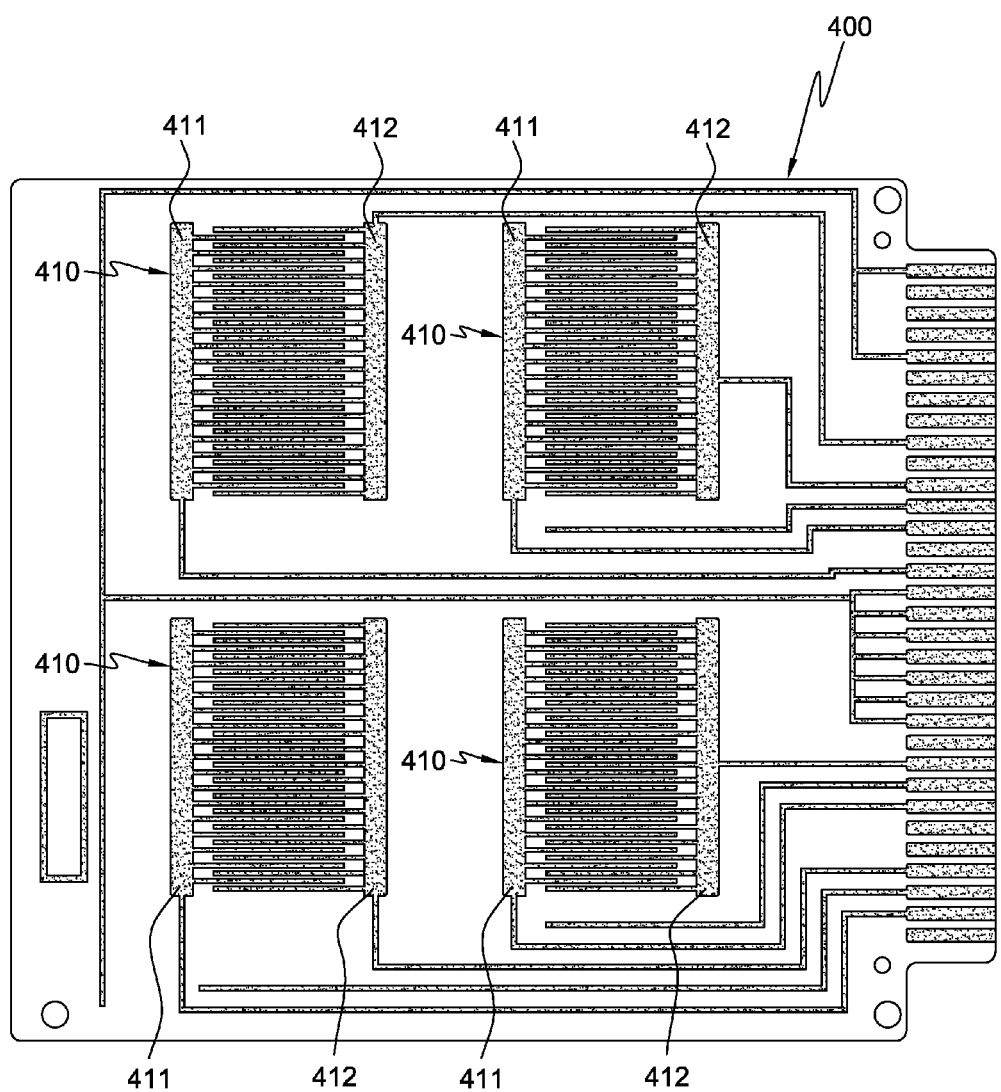
FIG. 4 depicts one embodiment of a dust coupon which may be employed to test for presence of conductive dust within a data center, in accordance with one or more aspects of the present invention.

FIG. 4 illustrates one embodiment of a dust detector or coupon, generally denoted 400, which could be employed with the early warning apparatus depicted (by way of example) in FIG. 3. As illustrated in FIG. 4, dust coupon 400 comprises multiple conductive dust sensors 410, each of which comprises two interdigitated conductive comb structures 411, 412. In operation, a detection voltage is applied across each set of interdigitated comb structures 411, 412, and the controller monitors, via one or more ammeters, for leakage current indicative of the presence of conductive dust. In this embodiment, dust coupon 400 is a planar structure and requires conductive dust to settle onto the comb structures in order to identify the presence of the conductive dust, which can be a disadvantage to early detection within an air-cooled electronics rack comprising a forced airflow through the rack.

Disclosed herein with reference to FIGS. 5A-6C are alternate embodiments of an early warning apparatus and dust detector for use within a data center, for example, within one or more air-cooled electronics racks within the data center. Generally stated, the monitoring apparatus comprises a dust detector, a voltage source, and a controller. The dust detector includes, in one embodiment, two opposing surfaces disposed in spaced, opposing relation with a gap therebetween to facilitate the passage of an airflow between the two opposing surfaces; and a conductive dust sensor disposed at one surface of the two opposing surfaces. The voltage source establishes an electrostatic field at least partially between the two opposing surfaces, which facilitates directing, at least in part, conductive particles in the airflow passing between the two opposing surfaces towards the conductive dust sensor; and the controller monitors for a leakage current within the conductive dust sensor and determines whether the leakage current exceeds a predetermined trigger level indicative of the presence of harmful conductive dust. Responsive to the leakage current exceeding the predetermined trigger level, the controller automatically indicates a conductive dust warning or alarm, and optionally, proactively controls one or more dehumidifiers within the data center or associated with the electronics rack in order to decrease relative humidity within the data center or the electronics rack, and thereby reduce conductivity of the detected conductive dust.

As noted, corrosive dust can arise from chemical particles that can form salts, and depending upon the humidity, result in a conductive bridge between exposed, adjacent lines of an electronic component. Leakage current trigger levels can be predetermined by, for example, applying a potentially harmful dust over interdigitated traces of a conductive dust sensor, with a detection voltage applied across the sensor, and an ammeter monitoring current to detect leakage across the interdigitated traces. With such a setup, humidity may be incrementally increased, and when the dust reaches its deliquescent point, the dust becomes conductive, and leakage current spikes. This concept is employed in setting the trigger level for identifying the existence of a potentially harmful or corrosive conductive dust within the electronic system, electronics rack, or data center at different humidity levels.

Figure 5B:
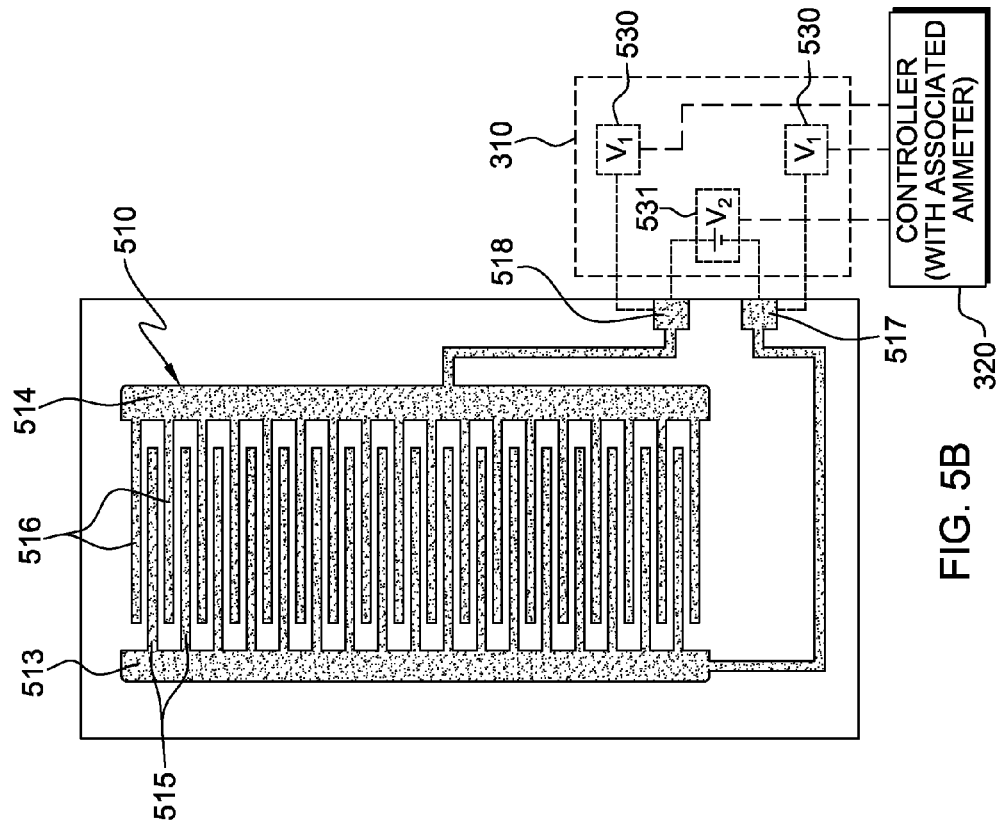
FIG. 5B depicts one embodiment of one surface of the two opposing surfaces of the dust detector of FIG. 5A, and illustrates one embodiment of a monitoring apparatus, including the conductive dust sensor thereof, in accordance with one or more aspects of the present invention.
Figure 5A:
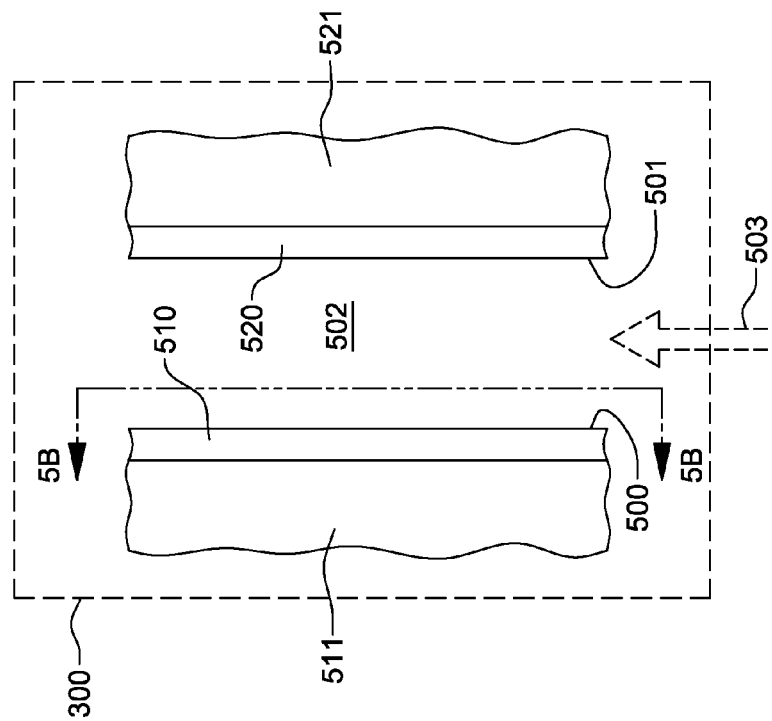
FIG. 5A is a cross-sectional elevational view of another embodiment of a dust detector, in accordance with one or more aspects of the present invention.
Figure 5C:
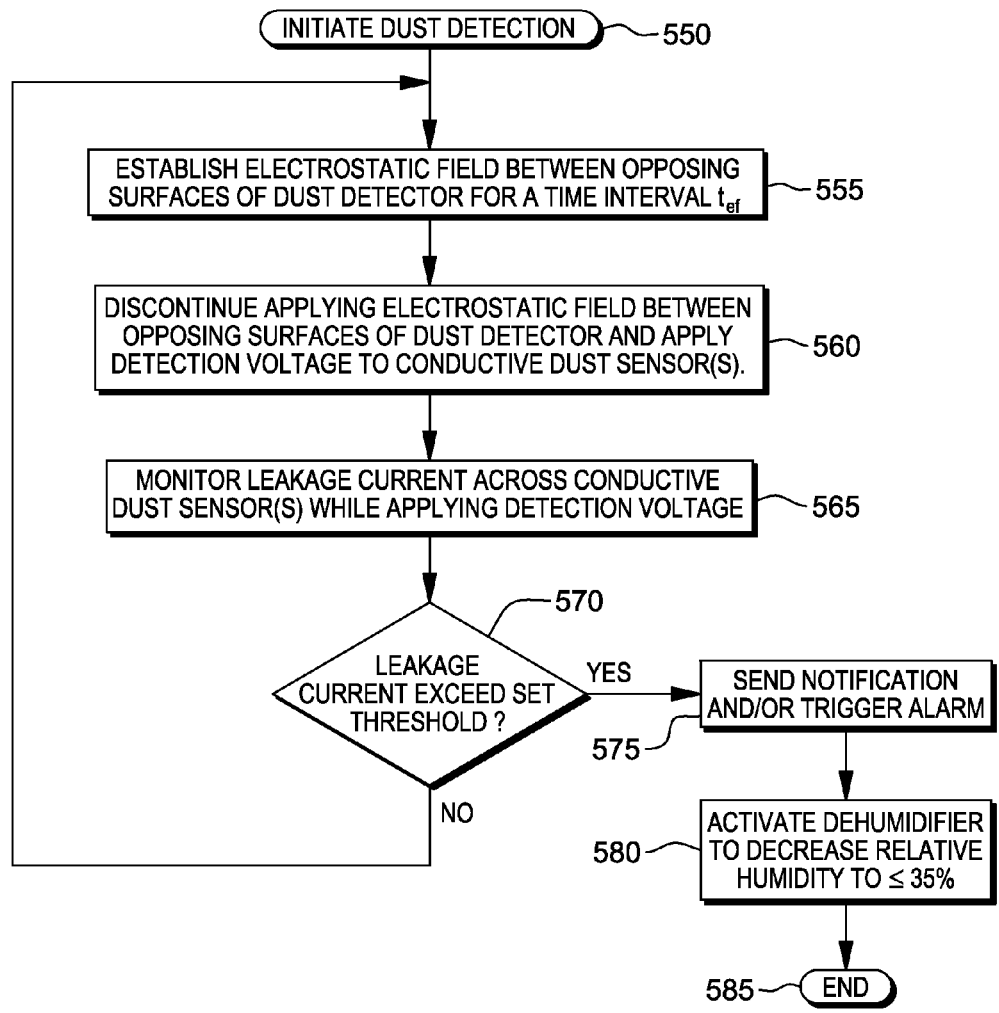
FIG. 5C depicts one embodiment of a process for conductive dust monitoring employing the detector and apparatus of FIGS. 5A & 5B, in accordance with one or more aspects of the present invention.

As noted, FIGS. 5A-5C depict one embodiment of an early warning apparatus and dust detector, in accordance with one or more aspects of the present invention. Referring initially to FIG. 5A, dust detector 300 comprises, in this embodiment, a first surface 500 and a second surface 501 disposed in spaced, close opposing relation with a gap 502 therebetween so that an airflow 503 can pass between the two opposing surfaces 500, 501. By way of example, the first and second surfaces 500, 501 may comprise parallel surfaces disposed approximately 0.1 inches apart. In the embodiment depicted, first surface 500 comprises (at least partially) a surface of a first conductive dust sensor 510 and second surface 501 comprises (at least partially) a surface of a second conductive dust sensor 520, which in one embodiment may be positioned opposite to each other within the two opposing surfaces 500, 501, and comprise similarly configured conductive dust sensors. In the depicted embodiment, first conductive dust sensor 510 is supported by a first substrate 511 and second conductive dust sensor 520 is supported by a second substrate 521.

Referring collectively to FIGS. 5A & 5B, first surface 500 is illustrated to comprise first conductive dust sensor 510, which in the embodiment depicted includes two interdigitated conductive comb structures 513, 514, comprising interdigitated conductive lines or traces 515, 516, upon which conductive dust (not shown) can settle, and cause a short circuit that results in a leakage current. Controller 320 monitors for a leakage current via one or more ammeters set to detect a predetermined trigger-level of current that is indicative of the presence of corrosive dust.

In one embodiment, controller 320 applies for a time interval $t_{ef}$, a first voltage ($V_1$) 530 to each of the contact pads 517, 518, electrically connected to the interdigitated conductive structures 513, 514. With voltage $V_1$ applied to the first conductive dust sensor 510 at the first surface 500, and a ground potential applied to the second conductive dust sensor 520 at the second surface 501 of the detector, an electrostatic field is established between the first and second surfaces 500, 501 in the gap 502 between the two opposing surfaces. This electrostatic field is (in one embodiment) substantially perpendicular to the direction of airflow 503 between the two opposing surfaces and facilitates directing, at least in part, the conductive dust particles to either first conductive dust sensor 510 or second conductive dust sensor 520, depending on the voltage and polarities applied to the respective sensors. In one example, 1K-10K volts may be applied between the first conductive dust sensor 510 and the second conductive dust sensor 520 across gap 502 between the two opposing surfaces 500, 501 to establish surface charges that facilitate the adsorption of charged dust particles.

After a period of time, the controller discontinues application of voltage $V_1$ to first conductive dust sensor 510, and applies a detection voltage $V_2$ 531 across each conductive dust sensor 510, 520 in order to monitor for a leakage current indicative of the presence of corrosive dust.

FIG. 5C depicts one embodiment of a process for monitoring for conductive dust employing an early warning apparatus and dust detector such as illustrated in FIGS. 5A & 5B. Upon initiating dust detection 550, the logic establishes an electrostatic field between the two opposing surfaces of the dust detector (upon which the sensors reside) for an electrostatic field time interval $t_{ef}$ 555. After time interval $t_{ef}$, processing discontinues applying the electrostatic field between the opposing surfaces of the dust detector and applies a second, detection voltage $V_2$ across each set of interdigitated conductive comb structures of the sensors 560. With the detection voltage applied across the interdigitated comb structures of each conductive dust sensor, the controller monitors for leakage current 565, and determines whether any detected leakage current exceeds a predetermined trigger level 570. If "no", then the controller re-establishes the electrostatic field between the opposing surfaces of the dust detector for time interval $t_{ef}$ 555 by, for example, re-applying voltage $V_1$ to the conductor(s) of one sensor, and ground potential to the other sensor. However, if one or more of the leakage currents exceeds the trigger level, then the controller issues a conductive dust warning or alarm 575, and optionally, activates one or more dehumidifiers within the data center (e.g., associated with the electronics rack) to decrease relative humidity of the airflow passing through the electronics rack to, for example, ≤35% 580, which completes dust detection 585 until the data center and/or rack(s) is serviced by a technician to remove the source of the conductive dust.

Figure 6B:
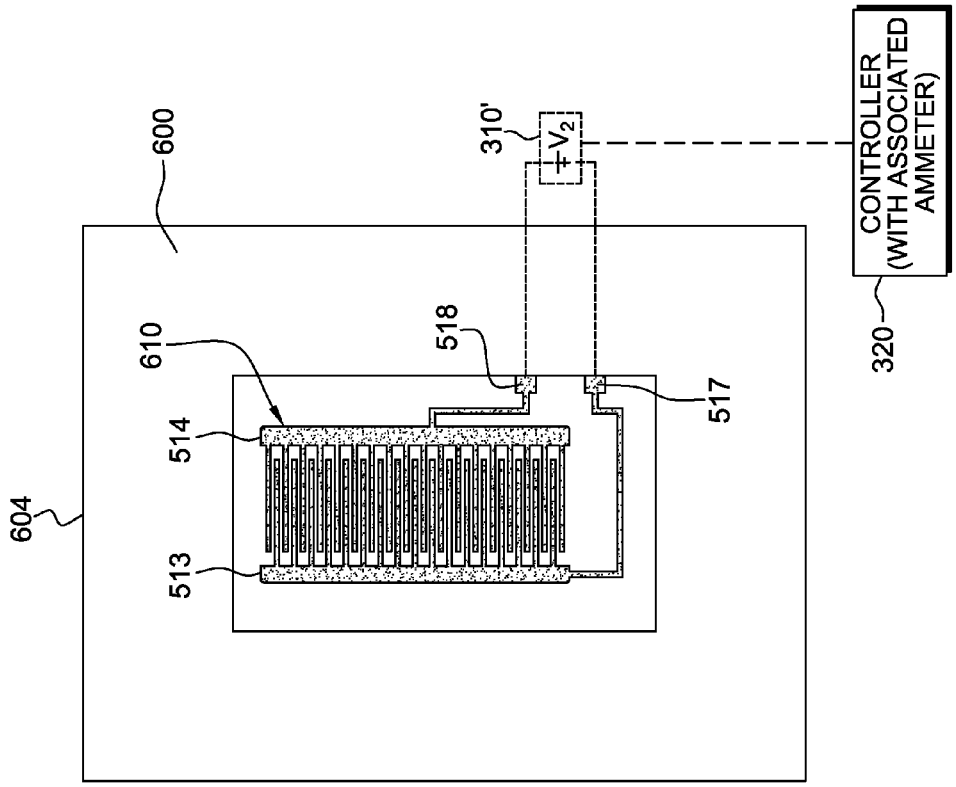
FIG. 6B depicts the monitoring apparatus of FIG. 6A, including one embodiment of one surface of the two opposing surfaces of the dust detector, in accordance with one or more aspects of the present invention.
Figure 6A:
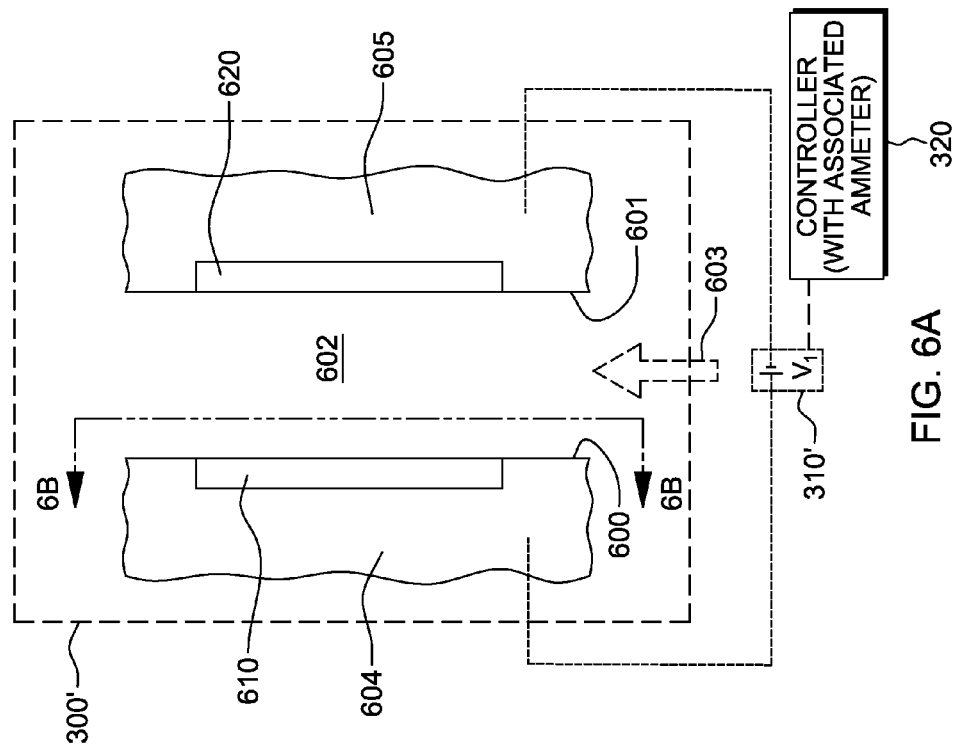
FIG. 6A depicts a monitoring apparatus, and a cross-sectional elevational view of another embodiment of a dust detector, in accordance with one or more aspects of the present invention.

FIGS. 6A & 6B depict an alternate embodiment of an early warning apparatus and dust detector 300', in accordance with one or more aspects of the present invention. As illustrated, dust detector 300' includes a first surface 600 and a second surface 601 disposed in spaced, close opposing relation with a gap 602 therebetween through which an airflow 603 passes. In this embodiment, a first conductive dust sensor 610 and a second conductive dust sensor 620 are embedded within, for example, first surface 600 and second surface 601, respectively. First surface 600 and second surface 601 are at least partially defined by a first conductive plate 604 and a second conductive plate 605, across which an electrostatic voltage $V_1$ is applied by voltage source 310' and controller 320. For example, voltage $V_1$ of 1K-10K Vs might be applied to first conductive plate 604 and ground potential to second conductive plate 605.

FIG. 6B illustrates a plan view of first conductive plate 604, with first surface 600 and embedded first conductive sensor 610. In this embodiment (and by way of example only), the first conductive sensor 610 is substantially identical to first conductive sensor 510 of the detector illustrated in FIGS. 5A & 5B. Real time monitoring is achieved by applying a second detection voltage $V_2$, via voltage source 310' and controller 320, across the two interdigitated conductive comb structures 513, 514 of the first conductive dust sensor 610. Note that, in this embodiment, the electrostatic field is established across the first and second conductive plates 604, 605, rather than across the first and second conductive dust sensors, as in the approach of FIGS. 5A & 5B. This advantageously allows for continuous monitoring of the airflow for early detection of harmful conductive dust particles.

Figure 6C:
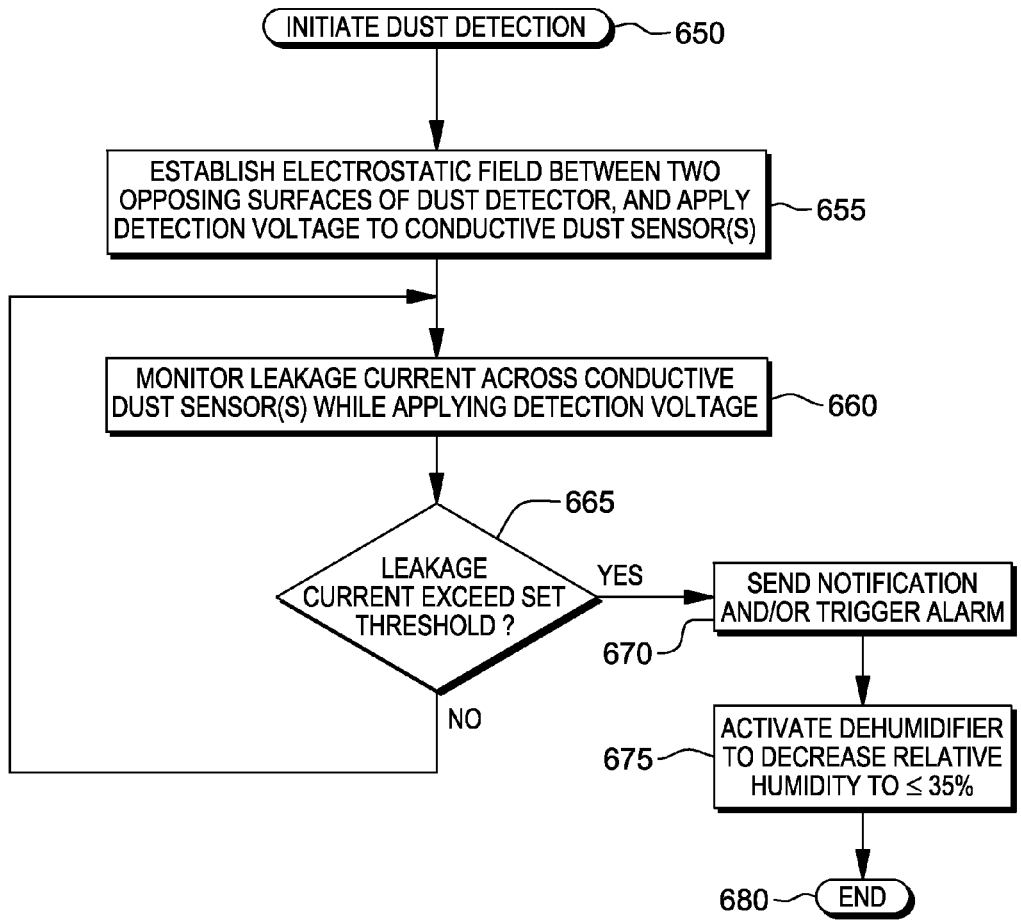
FIG. 6C depicts one embodiment of a process for conductive dust monitoring employing the apparatus of FIGS. 6A & 6B, in accordance with one or more aspects of the present invention.

FIG. 6C depicts one embodiment of logic implemented by a controller 320 employing dust detector 300' of FIGS. 6A & 6B. Upon initiating dust detection 650, the controller establishes an electrostatic field between the opposing surfaces of the dust detector and applies a detection voltage to the one or more conductive dust sensors 655. Processing then monitors for leakage current within the one or more conductive dust sensors 660, and determines whether the leakage current exceeds a trigger level indicative of the presence of harmful conductive dust 665, and if "no", continues to monitor leakage current within the conductive dust sensors 660. If "yes", then the controller sends a conductive dust warning or alarm 670, and optionally controls one or more dehumidifiers within the data center or the associated electronics rack to reduce relative humidity to, for example, below 35% 675, which completes 680 dust detection monitoring until a technician services the data center or electronics rack to reduce harmful dust in the airflow passing through the electronics rack.

Those skilled in the art will note from the above discussion that provided herein are various novel dust detectors and associated monitoring approaches which detect impingement of harmful dust on one or more conductive dust sensors of the detector. Enhancements to the dust detectors described herein may include roughening of the conductive traces or lines that are interdigitated in the interdigitated conductive comb structures of the sensor(s) to enhance the conductive surface area for dust adsorption. Similarly, the substrate upon which the conductive traces reside may be roughened in order to increase surface area for dust adsorption. This roughening can be achieved by, for example, chemical etching or by blasting the exposed surface of the sensor to roughen the surface. Other enhancements may include restricting the pitch of the traces in the sensors to as tight as practical, for example, to approximately 150 microns, or less today. Positioning the conductive dust sensors such that at least a portion of the data center air or airflow passing through the electronics rack is also pulled or forced between the opposing surfaces of the dust detector advantageously allows for the apparatus to function as an early warning system for potential harmful dust.

In one embodiment, the two opposing surfaces of the dust detector are separated by approximately 0.1 inches, and data center air is drawn into the gap between the two opposing surfaces of the dust detector, wherein the electrostatic field encourages conductive particles to adsorb onto one or the other of the conductive dust sensors disposed at the two opposing surfaces of the dust detector depending on the surface charge. Leakage current is monitored as a function of time, and if the leakage current exceeds a critical value (for example, spikes), then an alarm is triggered and the IT technician is notified that corrective action is required. Once harmful conductive dust is detected, damage to, for example, high powered traces within the electronics rack may be delayed by activating one or more dehumidifiers within the data center or electronics rack to drop the relative humidity of the airflow passing through the electronics rack to, for example, less than or equal to 35%. At or below this relative humidity, the dust is no longer conductive, and thus the threat of a burn event is reduced, if not eliminated. The IT technician will still need to be notified to take corrective action, but by actively dehumidifying the airflow, additional time is obtained to formulate and implement an appropriate response.

As will be appreciated by one skilled in the art, control aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system". Furthermore, control aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable signal medium may be any non-transitory computer readable medium that is not a computer readable storage medium and that can communicate, propagate, or transport a program for use by or in connection with an instruction execution system, apparatus or device.

A computer readable storage medium may be, for example, but not limited to, an electronic, magnetic, optical, electromagnetic, infrared or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Figure 7:
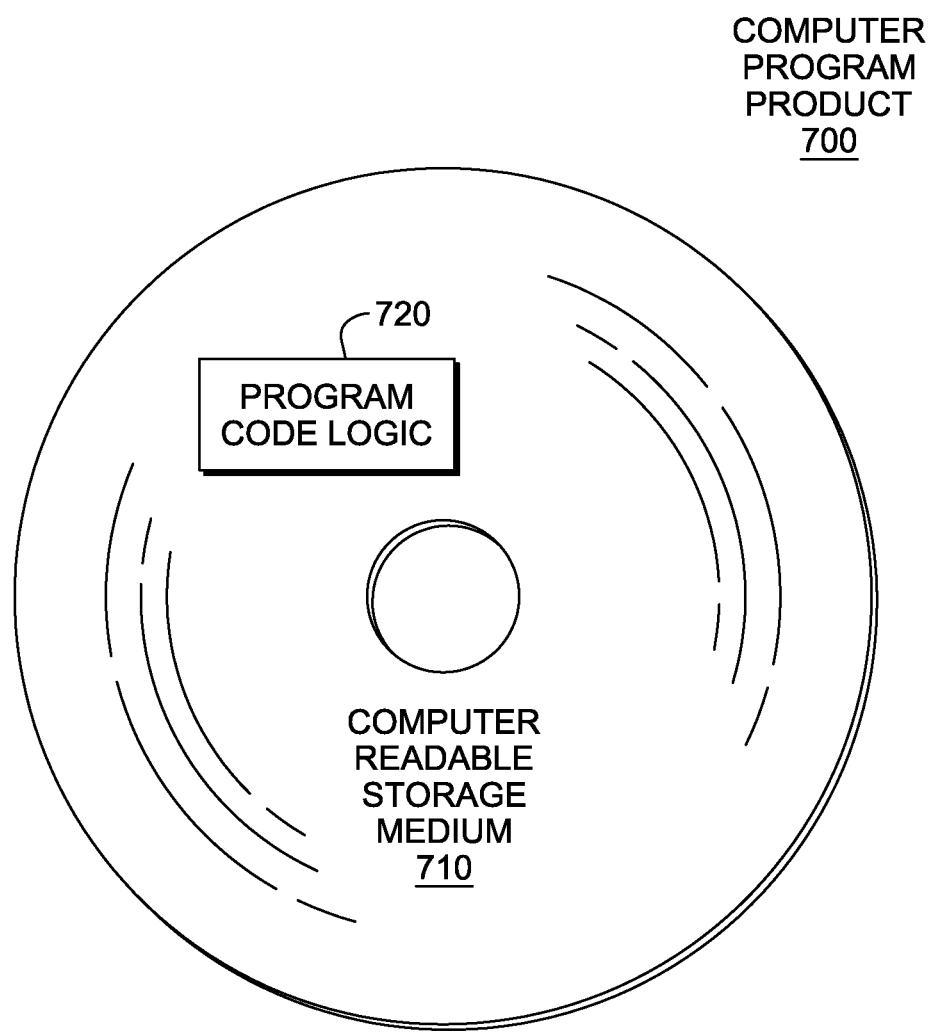
FIG. 7 depicts one embodiment of a computer program product to incorporate one or more aspects of the present invention.

Referring now to FIG. 7, in one example, a computer program product 700 includes, for instance, one or more computer readable storage media 710 to store computer readable program code means or logic 720 thereon to provide and facilitate one or more aspects of the present invention.

Program code embodied on a computer readable medium may be transmitted using an appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language, such as Java, Smalltalk, C++ or the like, and conventional procedural programming languages, such as the "C" programming language, assembler or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In addition to the above, one or more aspects of the present invention may be provided, offered, deployed, managed, serviced, etc. by a service provider who offers management of customer environments. For instance, the service provider can create, maintain, support, etc. computer code and/or a computer infrastructure that performs one or more aspects of the present invention for one or more customers. In return, the service provider may receive payment from the customer under a subscription and/or fee agreement, as examples. Additionally or alternatively, the service provider may receive payment from the sale of advertising content to one or more third parties.

In one aspect of the present invention, an application may be deployed for performing one or more aspects of the present invention. As one example, the deploying of an application comprises providing computer infrastructure operable to perform one or more aspects of the present invention.

As a further aspect of the present invention, a computing infrastructure may be deployed comprising integrating computer readable code into a computing system, in which the code in combination with the computing system is capable of performing one or more aspects of the present invention.

As yet a further aspect of the present invention, a process for integrating computing infrastructure comprising integrating computer readable code into a computer system may be provided. The computer system comprises a computer readable medium, in which the computer medium comprises one or more aspects of the present invention. The code in combination with the computer system is capable of performing one or more aspects of the present invention.

Although various embodiments are described above, these are only examples. For example, computing environments of other architectures can incorporate and use one or more aspects of the present invention. Additionally, the network of nodes can include additional nodes, and the nodes can be the same or different from those described herein. Also, many types of communications interfaces may be used.

Further, a data processing system suitable for storing and/or executing program code is usable that includes at least one processor coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/Output or I/O devices (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the form disclosed. Many modifications and variations will be apparent to those of ordinary skill in the art without departing from the scope and spirit of the invention. Certain embodiments were chosen and described in order to explain the principles of the invention and the practical application(s), and to enable others of ordinary skill in the art to understand the invention through the various embodiments and various modifications thereto which may be dependent on the particular uses contemplated.

What is claimed is:

1. An apparatus comprising:
   a dust detector comprising:
      two opposing surfaces disposed in spaced, opposing relation with a gap therebetween to facilitate passage of an airflow in-between the two opposing surfaces substantially parallel thereto;
      a conductive dust sensor, the conductive dust sensor comprising conductive lines exposed on one surface of the two opposing surfaces;
      a voltage source to establish an electrostatic field at least partially between the two opposing surfaces, the electrostatic field facilitating re-directing, at least in part, conductive dust particles in the airflow passing in-between the two opposing surfaces towards the conductive lines of the conductive dust sensor exposed on the one surface of the two opposing surfaces; and
      a controller configured to monitor for a leakage current within the conductive dust sensor due to conductive dust particles settling on the exposed conductive lines on the one surface of the two opposing surfaces within the gap between the two opposing surfaces, and to determine whether the leakage current exceeds a predetermined trigger level indicative of the presence of the conductive dust particles, and responsive to the leakage current exceeding the predetermined trigger level, to automatically indicate a conductive dust warning.

2. The apparatus of claim 1, wherein the electrostatic field between the two opposing surfaces is substantially perpendicular to a direction of the airflow passing in-between the two opposing surfaces.

3. The apparatus of claim 1, wherein the conductive dust sensor of the dust detector is a first conductive dust sensor exposed at a first surface of the two opposing surfaces, and the dust detector further comprises a second conductive dust sensor exposed at a second surface of the two opposing surfaces of the dust detector.

4. The apparatus of claim 3, wherein the controller controls the voltage source to apply a first voltage between the first conductive dust sensor and the second conductive dust sensor to establish the electrostatic field for a time interval t, then discontinues applying the first voltage between the first conductive dust sensor and the second conductive dust sensor and applies a second, detection voltage to the first conductive dust sensor and applies the second, detection voltage to the second conductive dust sensor to monitor for leakage current at the first conductive dust sensor due to conductive dust particles settling thereon or for leakage current at the second conductive dust sensor due to conductive dust particles settling thereon, and determines whether any leakage current exceeds the predetermined trigger level, and responsive to at least one leakage current exceeding the predetermined trigger level, the controller automatically indicates the conductive dust warning.

5. The apparatus of claim 4, wherein the first conductive dust sensor and the second conductive dust sensor each comprise two interdigitated conductive comb structures.

6. The apparatus of claim 5, wherein an exposed surface of the first conductive dust sensor and an exposed surface of the second conductive dust sensor each comprise a roughened surface that facilitates dust adsorption.

7. The apparatus of claim 1, further comprising a dehumidifier, and wherein responsive to the leakage current exceeding the predetermined trigger level, the controller is configured to automatically control the dehumidifier to decrease relative humidity within a data center containing the apparatus.

8. The apparatus of claim 1, wherein the dust detector further comprises a first conductive plate and a second conductive plate, the first conductive plate defining at least partially a first surface of the two opposing surfaces and the second conductive plate defining at least partially a second surface of the two opposing surfaces, and wherein the voltage source applies a first voltage between the first conductive plate and the second conductive plate to establish the electrostatic field upstream of the conductive dust sensor in a direction of airflow passage in-between the first and second surfaces of the two opposing surfaces.

9. The apparatus of claim 8, wherein the conductive dust sensor is a first conductive dust sensor positioned on the first conductive plate.

10. The apparatus of claim 9, wherein the dust detector further comprises a second conductive dust sensor positioned on the second conductive plate.

11. The apparatus of claim 10, wherein the first conductive dust sensor and the second conductive dust sensor each comprise two interdigitated conductive comb structures, and an exposed surface of the first conductive dust sensor and an exposed surface of the second conductive dust sensor each comprise a roughened surface that facilitates dust adsorption, and wherein the voltage source applies a second, detection voltage to the first conductive dust sensor to monitor for leakage current at the first conductive dust sensor due to conductive dust sensor settling thereon and applies the second, detection voltage to the second conductive dust sensor to monitor for leakage current at the second conductive dust sensor due to conductive dust particles settling thereon.

12. An electronics rack comprising:
at least one air-moving device to establish an airflow through the electronics rack; and
a monitoring apparatus associated with the electronics rack, the monitoring apparatus comprising:
at least one dust detector, said at least one dust detector comprising:
two opposing surfaces disposed in spaced, opposing relation with a gap therebetween to facilitate passage of an airflow in-between the two opposing surfaces substantially parallel thereto;
a conductive dust sensor, the conductive dust sensor comprising conductive lines and being exposed on one surface of the two opposing surfaces;
a voltage source to establish an electrostatic field at least partially between the two opposing surfaces, the electrostatic field facilitating re-directing, at least in part, conductive dust particles in the airflow passing in-between the two opposing surfaces towards the conductive lines of the conductive dust sensor exposed on the one surface of the two opposing surfaces; and
a controller configured to monitor for a leakage current within the conductive dust sensor due to conductive dust particles settling on the exposed conductive lines on the one surface of the two opposing surfaces within the gap between the two opposing surfaces, and to determine whether the leakage current exceeds a predetermined trigger level indicative of the presence of the conductive dust particles, and responsive to the leakage current exceeding the predetermined trigger level, to automatically indicate a conductive dust warning.

13. The electronics rack of claim 12, wherein the conductive dust sensor of each dust detector is a first conductive dust sensor exposed at a first surface of the two opposing surfaces, and each dust detector further comprises a second conductive dust sensor exposed at a second surface of the two opposing surfaces, and wherein the controller controls the voltage source to apply a first voltage between the first conductive dust sensor and the second conductive dust sensor to establish the electrostatic field for a time interval t, then discontinues applying the first voltage between the first conductive dust sensor and the second conductive dust sensor and applies a second, detection voltage to the first conductive dust sensor and applies the second, detection voltage to the second conductive dust sensor to monitor for leakage current at the first conductive dust sensor due to conductive dust particles settling thereon or for leakage current at the second conductive dust sensor due to conductive dust particles settling thereon, and determines whether any monitored leakage current exceeds the predetermined trigger level and responsive to at least one leakage current exceeding the predetermined trigger level, the controller automatically indicates the conductive dust warning.

14. The electronics rack of claim 13, wherein the first conductive dust sensor and the second conductive dust sensor each comprise two interdigitated conductive comb structures, and wherein an exposed surface of the first conductive dust sensor and an exposed surface of the second conductive dust sensor each comprises a roughened surface that facilitates dust adsorption.

15. The electronics rack of claim 12, wherein the monitoring apparatus further comprises a dehumidifier, and wherein responsive to the leakage current exceeding the predetermined trigger level, the controller is configured to automatically control the dehumidifier to decrease relative humidity within a data center containing the electronics rack.

16. The electronics rack of claim 12, wherein the dust detector further comprises a first conductive plate and a second conductive plate, the first conductive plate defining at least partially a first surface of the two opposing surfaces and the second conductive plate defining at least partially a second surface of the two opposing surfaces, and wherein the voltage source applies a first voltage between the first conductive plate and the second conductive plate to establish the electrostatic field upstream of the conductive dust sensor in a direction of airflow passage in-between the first and second surfaces of the two opposing surfaces.

17. The electronics rack of claim 16, wherein the conductive dust sensor is a first conductive dust sensor positioned on the first conductive plate, and each dust detector further comprises a second conductive dust sensor positioned on the second conductive plate, wherein the first conductive dust sensor and the second conductive dust sensor each comprises two interdigitated conductive comb structures, and an exposed surface of the first conductive dust sensor and an exposed surface of the second conductive dust sensor each comprises a roughened surface that facilitates dust adsorption, and wherein the voltage source applies a second, detection voltage to the first conductive sensor to monitor for leakage current at the first conductive dust sensor due to conductive dust particles settling thereon and applies the second, detection voltage to the second conductive dust sensor to monitor for leakage current at the second conductive dust sensor due to conductive dust particles settling thereon.

18. A monitoring method comprising:
associating a dust detector with an electronics rack, the dust detector comprising:
two opposing surfaces disposed in spaced, opposing relation with a gap therebetween to facilitate passage of an airflow in-between the two opposing surfaces substantially parallel thereto:
a conductive dust sensor, the conductive dust sensor comprising conductive lines exposed on one surface of the two opposing surfaces; and
establishing an electrostatic field at least partially between the two opposing surfaces, the electrostatic field facilitating re-directing, at least in part, conductive dust particles in the airflow passing in-between the two opposing surfaces towards the conductive lines of the conductive dust sensor exposed on the one surface of the two opposing surfaces; and monitoring, via a controller, for a leakage current within the conductive dust sensor indicative of the presence of conductive dust particles settling on the exposed conductive lines on the one surface of the two opposing surfaces within the gap between the two opposing surfaces, and determining whether the leakage current exceeds a predetermined trigger level; and responsive to the leakage current exceeding the predetermined trigger level, automatically indicating a conductive dust warning.

19. The monitoring method of claim 18, wherein the conductive dust sensor of the dust detector is a first conductive dust sensor exposed at a first surface of the two opposing surfaces, and the dust detector further comprises a second conductive dust sensor exposed at a second surface of the two opposing surfaces of the dust detector, and wherein the method further comprises controlling the voltage source to apply a first voltage between the first conductive dust sensor and the second conductive dust sensor to establish the electrostatic field for a time interval t, then discontinuing applying the first voltage between the first conductive dust sensor and the second conductive dust sensor and applying a second, detection voltage to the first conductive dust sensor and applying the second, detection voltage to the second conductive dust sensor to monitor for leakage current at the first conductive dust sensor due to conductive dust particles settling thereon or for leakage current at the second conductive dust sensor due to conductive dust particles settling thereon, and determining whether any leakage current exceeds the predetermined trigger level, and responsive to at least one leakage current exceeding the predetermined trigger level, then automatically indicating the conductive dust warning.

20. The monitoring method of claim 18, further comprising, responsive to the leakage current exceeding the predetermined trigger level, automatically dehumidifying a data center containing the electronics rack to decrease relative humidity within the data center, and thereby conductivity of any conductive dust entrained within the airflow.

\* \* \* \* \*